United States Patent
Kang et al.

(10) Patent No.: US 9,574,999 B2
(45) Date of Patent: Feb. 21, 2017

(54) OUTDOOR UNIT OF AIR CONDITIONER AND METHOD OF CONTROLLING THE SAME

(71) Applicant: Samsung Electronics Co., Ltd., Suwon-si (KR)

(72) Inventors: Tae Woo Kang, Suwon-si (KR); Han Suk Lee, Incheon (KR); Wang Byung Chae, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/860,440

(22) Filed: Sep. 21, 2015

(65) Prior Publication Data

US 2016/0091425 A1 Mar. 31, 2016

(30) Foreign Application Priority Data

Sep. 25, 2014 (KR) .......................... 10-2014-0128679

(51) Int. Cl.
| | |
|---|---|
| *G01N 21/55* | (2014.01) |
| *G01B 11/14* | (2006.01) |
| *F24F 1/06* | (2011.01) |
| *F24F 1/50* | (2011.01) |
| *F24F 1/58* | (2011.01) |
| *G01W 1/14* | (2006.01) |

(52) U.S. Cl.
CPC ............... *G01N 21/55* (2013.01); *F24F 1/06* (2013.01); *F24F 1/50* (2013.01); *F24F 1/58* (2013.01); *G01B 11/14* (2013.01); *G01W 1/14* (2013.01)

(58) Field of Classification Search
CPC ..... G01B 11/14; G01F 23/2921; G01J 1/0233; G01J 1/0242; G01J 1/0266; G01J 2001/4266; G01N 21/55; G01N 24/08; G01N 24/081

See application file for complete search history.

(56) References Cited

U.S. PATENT DOCUMENTS

| | | | |
|---|---|---|---|
| 2011/0219868 A1* | 9/2011 | Lane | G01F 23/2921 73/170.21 |
| 2015/0114014 A1* | 4/2015 | Choi | F24F 1/06 62/89 |
| 2015/0330644 A1* | 11/2015 | Jeung | F24F 11/0076 62/186 |
| 2016/0084986 A1* | 3/2016 | Zach | G01V 3/00 219/502 |

FOREIGN PATENT DOCUMENTS

| | | | |
|---|---|---|---|
| JP | 2000248693 | * | 9/2000 |
| KR | 20060093317 A | | 8/2006 |

* cited by examiner

*Primary Examiner* — Michael P Stafira

(57) ABSTRACT

Provided are an outdoor unit of an air conditioner that detects snow that piles up on the outdoor unit of the air conditioner and a method of controlling the same. When a detection device is installed in the outdoor unit and snow piles up in a snow cover detection area included in the detection device, it is detected using an optical sensor whether snow cover occurs. A value detected by the optical sensor is transmitted to a controller, and the controller compares the value with a default value, and when the controller receives a value different from the default value, the controller controls a fan driving unit to drive a fan. Wind generated by driving the fan removes snow that piles up in the snow cover detection area, a fan guard and a discharge port to prevent the fan from malfunctioning due to accumulated snow.

20 Claims, 14 Drawing Sheets

OUTDOOR UNIT OF AIR CONDITIONER AND METHOD OF CONTROLLING THE SAME

CROSS-REFERENCE TO RELATED APPLICATION(S) AND CLAIM OF PRIORITY

The present application is related to and claims the benefit of Korean Patent Application No. 10-2014-0128679, filed on Sep. 25, 2014 in the Korean Intellectual Property Office, the disclosure of which is incorporated herein by reference.

TECHNICAL FIELD

Embodiments of the present disclosure relate to an outdoor unit of an air conditioner and a method of controlling the same, and more particularly, for snow cover detection when snow piles up on an outdoor unit and a method of controlling the same.

BACKGROUND

In general, air conditioners are devices that control indoor air using a cooling cycle. Air conditioners cool an indoor space by intaking hot indoor air, performing heat exchange between the hot indoor air and a low-temperature refrigerant and then discharging the heat-exchanged air to the indoor space, or heats an indoor space by intaking low-temperature indoor air, performing heat exchange between the low-temperature indoor air and a high-temperature refrigerant, and then discharging the heat-exchanged air to the indoor space.

Air conditioners can cool or heat air of the indoor space through a cooling cycle in which the air is circulated through a compressor, an outdoor heat exchanger (condenser), an expansion valve, and an indoor heat exchanger (evaporator) in a forward or backward direction. The compressor provides a gaseous refrigerant in a high-temperature high-pressure state, and the condenser provides a refrigerant in a liquid state in a room-temperature high-pressure state. The expansion valve decompresses the liquid refrigerant in a room-temperature high-pressure state, and the evaporator evaporates the decompressed gaseous refrigerant in a low-temperature state.

In a separation type air conditioner in which an outdoor unit and an indoor unit of the air conditioner are installed to be separated from each other, the compressor and the outdoor heat exchanger are provided for the outdoor unit.

The outdoor unit is disposed outside a building and is exposed to an external environment. In winter, when there is a large amount of snow cover, the outdoor unit can freeze due to snow or rain and does not operate.

SUMMARY

To address the above-discussed deficiencies, it is a primary object to provide, for use in an outdoor unit of an air conditioner having an improved structure including a measurement device that can detect snow cover piling up on the outdoor unit, and a method of controlling the same.

Another aspect of the present disclosure provides an outdoor unit of an air conditioner having an improved structure in which, when snow cover piling up on the outdoor unit is detected, the outdoor unit is operated, and a method of controlling the same.

Additional aspects of the disclosure will be set forth in part in the description which follows and, in part, will be obvious from the description, or is learned by practice of the disclosure.

In accordance with one aspect of the present disclosure, an air conditioner includes: an outdoor unit of an air conditioner, the outdoor unit including: an outdoor unit main body including a fan and a discharge port; and a detection device installed in the outdoor unit main body to detect snow that piles up on the outdoor unit main body, wherein the detection device includes: an optical sensor including a light-emitting unit and a light-receiving unit; a reflecting plate disposed to be spaced from the optical sensor and configured to reflect optical signals radiated from the light-emitting unit; and a snow cover detection area disposed between the optical sensor and the reflecting plate.

The snow cover detection area is formed in an upper side of the discharge port that is a ventilation path of the fan so that snow that piles up in the snow cover detection area is removed based on an operation of the fan.

The snow cover detection area includes a plurality of ribs disposed on a bottom end of the snow cover detection area so that wind generated by an operation of the fan is able to pass through the snow cover detection area and remove accumulated snow.

The detection device includes: an optical sensor housing on which the optical sensor is seated; and a pair of frames disposed to extend from one side of the optical sensor housing to the reflecting plate so that the optical sensor housing and the reflecting plate are connected to each other.

The snow cover detection area is disposed between the optical sensor housing and the reflecting plate to extend from one side of each of the frames.

Each of the frames further includes a coupling portion that extends to a lower side of the frame and is coupled to a fan guard so that one side of the detection device and the fan guard provided for the discharge port of the outdoor unit are coupled to each other.

The coupling portion is disposed to have a shape of a hook facing the lower side of the frame so that the fan guard and the detection device are able to be separated from each other.

The optical sensor housing includes: a transparent member disposed to correspond to a front surface of the optical sensor; and a fixing member disposed to fix the front surface of the optical sensor and the transparent member.

The optical sensor housing further includes a plate that extends from a top end of the optical sensor housing to a side that a front surface of the optical sensor faces so as to protect the front surface of the optical sensor.

The plate includes a flange that protrudes to an upper side of a circumferential surface of the plate and is disposed to have a shape of a slope, one end of which facing an outside of the plate is lifted upward.

The plate includes a drainage groove disposed from a side that contacts the optical sensor housing toward a lower side of the optical sensor housing so that water that remains in the plate is drained toward a bottom end of the optical sensor housing.

The optical sensor housing further includes a fixing portion disposed to be fixed to an upper side of the outdoor unit.

The fixing portion includes: a bracket that is bent and extends from a lower side of the optical sensor housing to face the upper side of the outdoor unit; and a plurality of slits through which the bracket passes and screw-coupled to the outdoor unit.

In accordance with another aspect of the present disclosure, an outdoor unit for an air conditioner includes: an outdoor unit main body including a fan and a discharge port; and a detection device installed to be separated from the outdoor unit main body and configured to detect snow that piles up on the outdoor unit main body, wherein the detection device includes: an optical sensor including a light-emitting unit and a light-receiving unit; and a snow cover detection area disposed on an optical path in which optical signals radiated from the light-emitting unit reach the light-receiving unit.

The light-emitting unit and the light-receiving unit are disposed to be spaced from each other, and the snow cover detection area is disposed between the light-emitting unit and the light-receiving unit.

The snow cover detection area includes a plurality of ribs that are disposed on an upper portion of the discharge port so that accumulated snow is able to be removed based on an operation of the fan and that are disposed on a bottom end of the snow cover detection area so that wind generated by the fan is able to remove snow.

The outdoor unit further includes a reflecting plate disposed so that the optical path formed between the light-emitting unit and the light-receiving unit is changed, by reflecting optical signals generated by the light-emitting unit.

In accordance with still another aspect of the present disclosure, a method of controlling an outdoor unit of an air conditioner including an outdoor unit main body including a fan, includes: radiating optical signals toward a reflecting plate using a light-emitting unit of an optical sensor; receiving the radiated optical signals, after reflecting off the reflecting plate, using a light-receiving unit of the optical sensor and measuring a distance of light movement; comparing the measured distance with a default value that is a distance value between the light-emitting unit and the reflecting plate; and when the measured distance is different from the default value or optical signals are not received by the light-receiving unit, driving the fan.

The method further includes measuring time when a state in which the measured distance is different from the default value or no optical signals are received, is maintained.

When the measured time is equal to or greater than a reference time, the fan is driven.

The method further includes stopping the fan when the optical signals received by the light-receiving unit regain the default value after the fan is driven.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 13, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system. Hereinafter, exemplary embodiments of the present disclosure will be described in detail with reference to the accompanying drawings.

Figure 1:
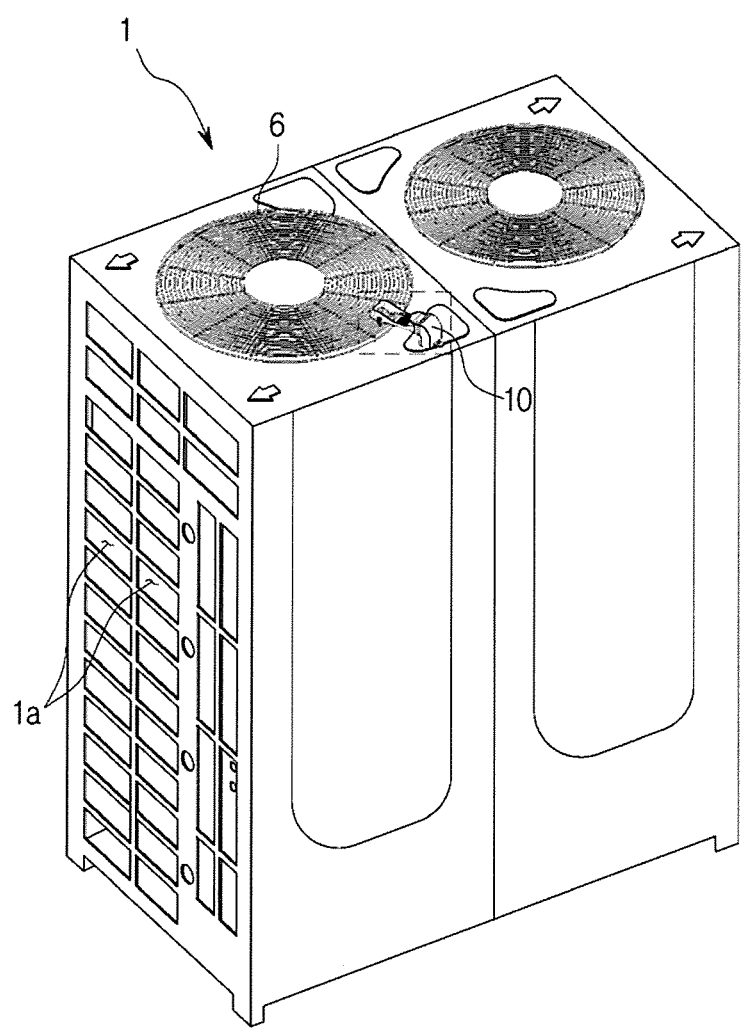
FIG. 1 illustrates an outdoor unit of an air conditioner according to various embodiments of the present disclosure.
Figure 2:
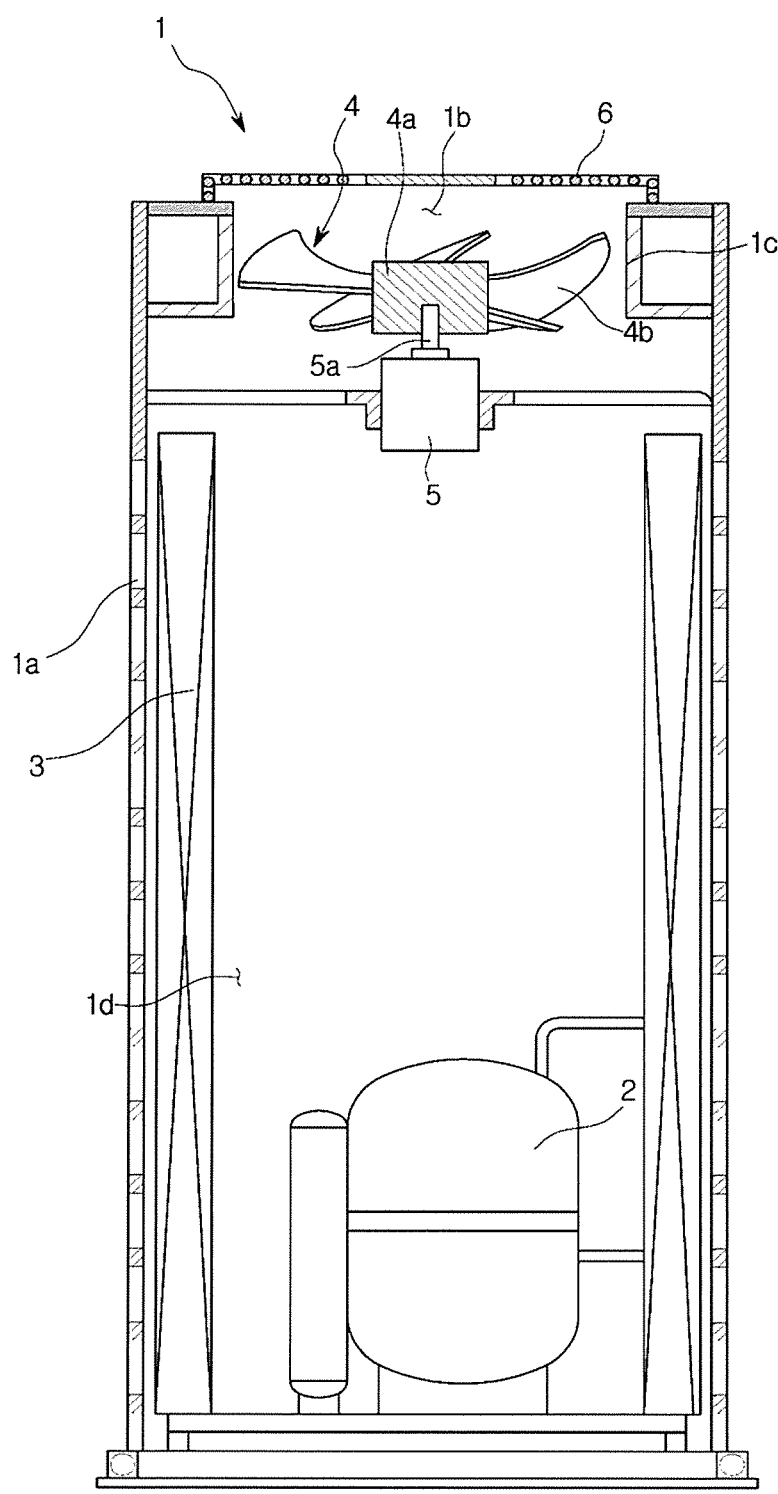
FIG. 2 illustrates a main body of the outdoor unit of the air conditioner according to various embodiments of the present disclosure.
Figure 3:
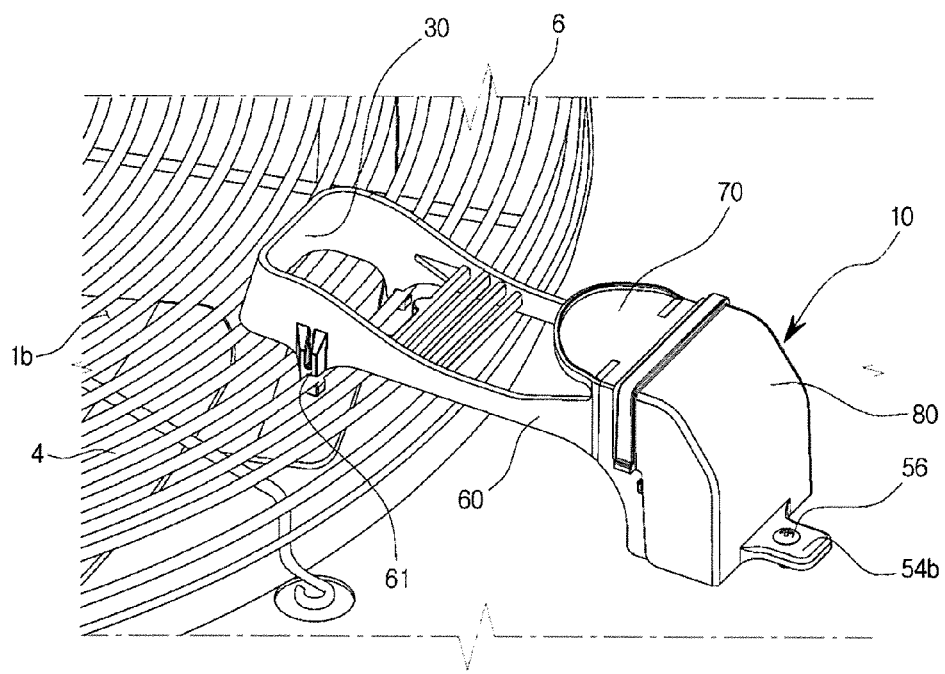
FIG. 3 illustrates a partial area of FIG. 1 that is a perspective view of an outdoor unit of an air conditioner according to various embodiments of the present disclosure.

An outdoor unit of an air conditioner according to various embodiments of the present disclosure includes an outdoor unit main body 1 that forms an exterior of the outdoor unit, a compressor 2 that is installed under the outdoor unit main body 1 and compresses a refrigerant, an outdoor heat exchanger 3 that exchanges heat with outdoor air, a fan 4 that allows outdoor air to pass through the outdoor unit main body 1 and exchanges heat with the outdoor heat exchanger 3, and a driving motor 5 that rotates the fan 4, as illustrated in FIGS. 1 through 3.

The outdoor unit main body 1 includes an inhalation port 1a through which air is inhaled into the outdoor unit main body 1, and a discharge port 1b through which air heat-exchanged with the outdoor heat exchanger 3 is discharged into an outdoor space.

In the current embodiment, the inhalation port 1a is disposed in a side of the outdoor unit main body 1, and the discharge port 1b is disposed in a top surface of the outdoor unit main body 1. In addition, the above-described fan 4 is installed in an upper portion of the outdoor unit main body 1, and the discharge port 1b is disposed in a top end of the outdoor unit main body 1, and the outdoor unit main body 1 further includes a bell mouse portion 1c that guides air discharged from the outdoor unit main body 1.

The compressor 2 is installed in an electronic device compartment 1d disposed to be partitioned in a lower portion of the outdoor unit main body 1, and compresses the refrigerant transferred from the outdoor heat exchanger 3 or an indoor heat exchanger (not shown) of an indoor unit (not shown).

The outdoor heat exchanger 3 is disposed inside the inhalation port 1a and exchanges heat with air introduced through the inhalation port 1a.

The fan 4 is disposed so that a shaft of the fan 4 is disposed in the above-described bell mouse portion 1c to face in a vertical direction and air is discharged toward the discharge port 1b disposed in an upper side of the outdoor unit main body 1.

The fan 4 includes a hub portion 4a, which has a shaft 5a of the driving motor 5 installed in the center of the fan 4 and to which a rotational force is transferred from the driving motor 5, and a plurality of wing portions 4b that extend outward in a radial direction from the hub portion 4a and is disposed to be spaced from each other in a circumferential direction, as illustrated in FIG. 2.

A fan guard 6 is disposed at an upper side of the discharge port 1b to correspond to the discharge port 1b to protect the fan 4. In detail, the fan guard 6 is disposed to have a circular grill shape that covers the discharge port 1b and the bell mouse portion 1c.

The detection device 10 is disposed on the top end of the outdoor unit main body 1. In detail, the detection device 10 is disposed in the fan guard 6 and an upper portion of the outdoor unit main body 1.

The detection device 10 includes an optical sensor 20 and a reflecting plate 30 that is disposed to reflect optical signals generated in the optical sensor 20 and to transmit the reflected optical signals to the optical sensor 20 again.

Figure 4:
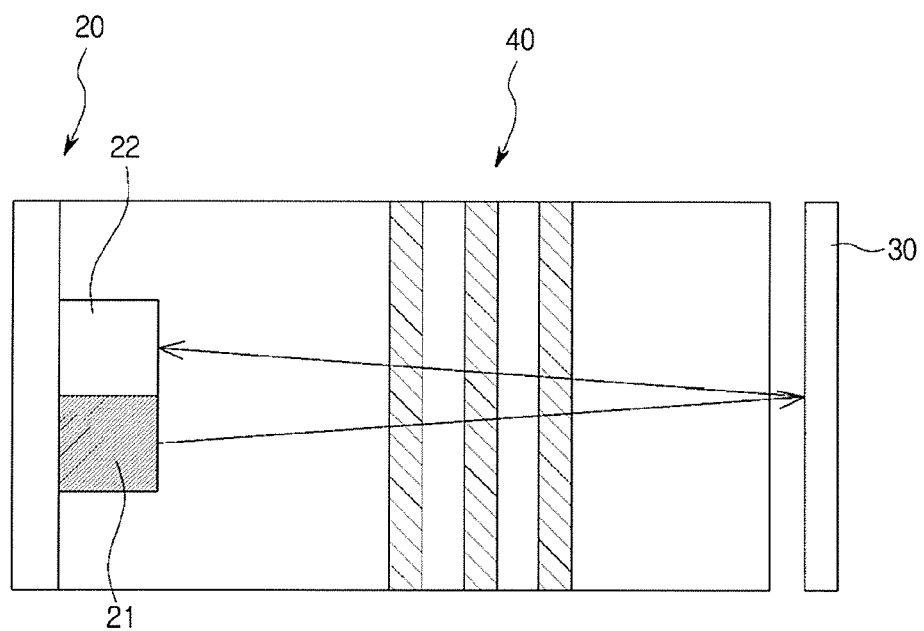
FIG. 4 illustrates a concept in which a default value is detected by a detection device installed in an outdoor unit main body according to various embodiments of the present disclosure.

As illustrated in FIGS. 4 and 5, the optical sensor 20 includes a light-emitting unit 21 and a light-receiving unit 22. The light-emitting unit 21 radiates optical signals, and the light-receiving unit 22 collects the optical signals radiated from the light-emitting unit 21 and measures a value of the optical signals.

A position sensing device (PSD) sensor is used as the optical sensor 20 according to various embodiments of the present disclosure. The light-emitting unit 21 and the light-receiving unit 22 of the PSD sensor are disposed in parallel with a front surface of the PSD sensor.

The PSD sensor calculates a value of the optical signals that are received by the light-receiving unit 22 when infrared signals generated in the light-emitting unit 21 are reflected in a particular position, and measures a distance between the outdoor unit main body 1 and the particular position of the reflecting plate 30 in which reflection of the optical signals is performed.

The reflecting plate 30 is disposed to have a shape of a plate that reflects the optical signals. When the optical signals are reflected from a surface of the reflecting plate 30, surface roughness of the reflecting plate 30 is decreased so that interference, such as diffused reflection, does not occur.

The reflecting plate 30 is disposed to be spaced from the optical sensor 20.

In detail, the reflecting plate 30 is disposed in the range of a distance at which the optical signals generated in the light-emitting unit 21 is reflected by the reflecting plate 30 and is input to the light-receiving unit 22.

The optical signals radiated from the light-emitting unit 21 form a predetermined incidence angle and a predetermined reflection angle, are reflected by the reflecting plate 30 and are received by the light-receiving unit 22. When the reflecting plate 30 is disposed adjacent to the optical sensor 20, the optical signals cannot be received by the light-receiving unit 22 due to the incidence angle and the reflection angle of the optical signals. The optical sensor 20 may not measure the value of the optical signals.

As illustrated in FIG. 4, the optical signals radiated from the light-emitting unit 21 toward the reflecting plate 30 are received by the light-receiving unit 22. The value of the optical signals collected by the light-receiving unit 22 without an interference between the optical sensor 20 and the reflecting plate 30 becomes a default value.

Figure 5A:
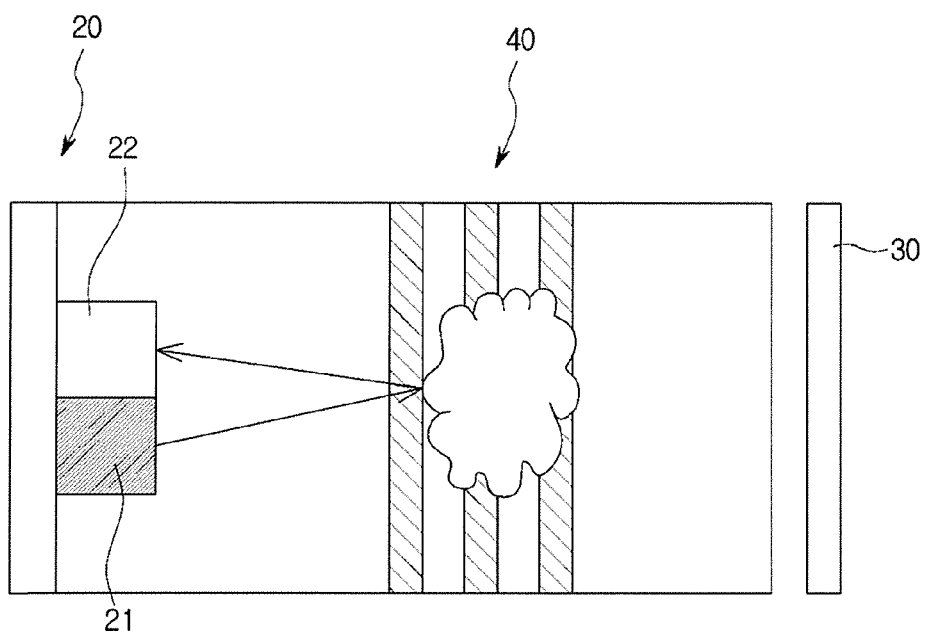
FIGS. 5A and 5B illustrate concepts in which a value rather than a default value is detected by the detection device installed in the outdoor unit main body according to various embodiments of the present disclosure.

Contrary to this, as illustrated in FIG. 5A, when the optical signals are reflected by the reflecting plate 30, are interfered by another material and are reflected by another material rather than the reflecting plate 30, the optical signals input to the light-receiving unit 22 have a value that is different from the default value (a).

Figure 5B:
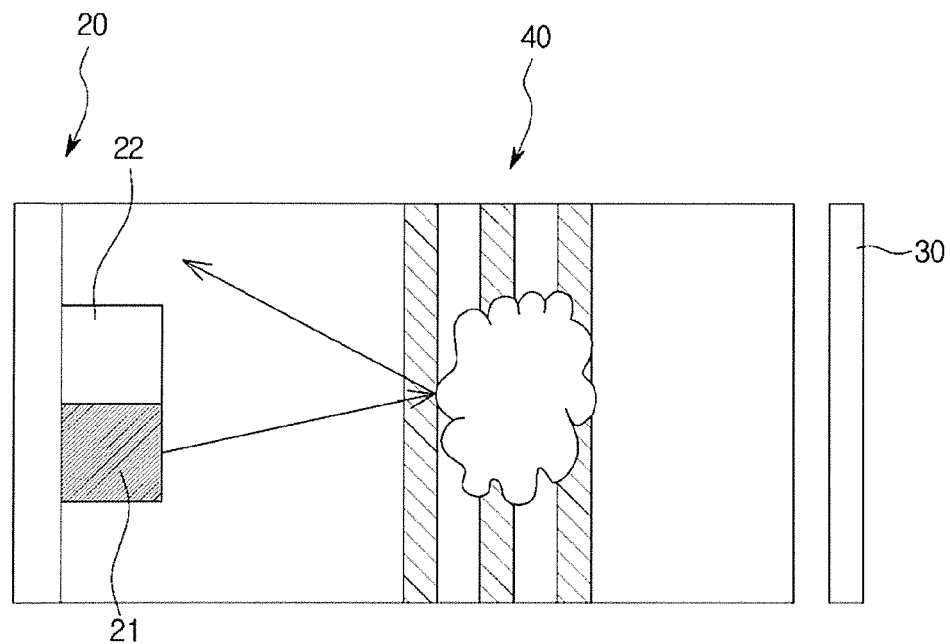
Figure 6:
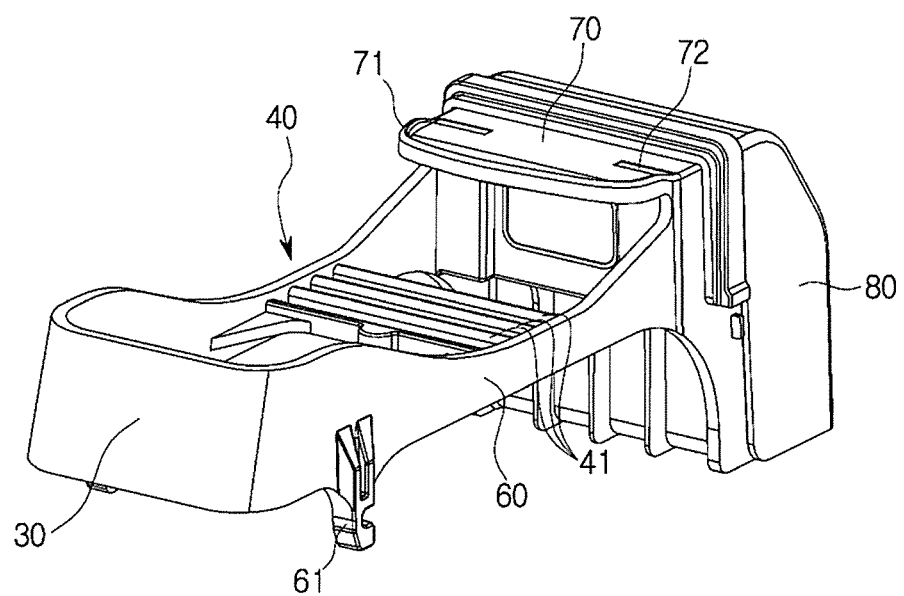
FIG. 6 illustrates a configuration of the detection device according to various embodiments of the present disclosure.
Figure 7:
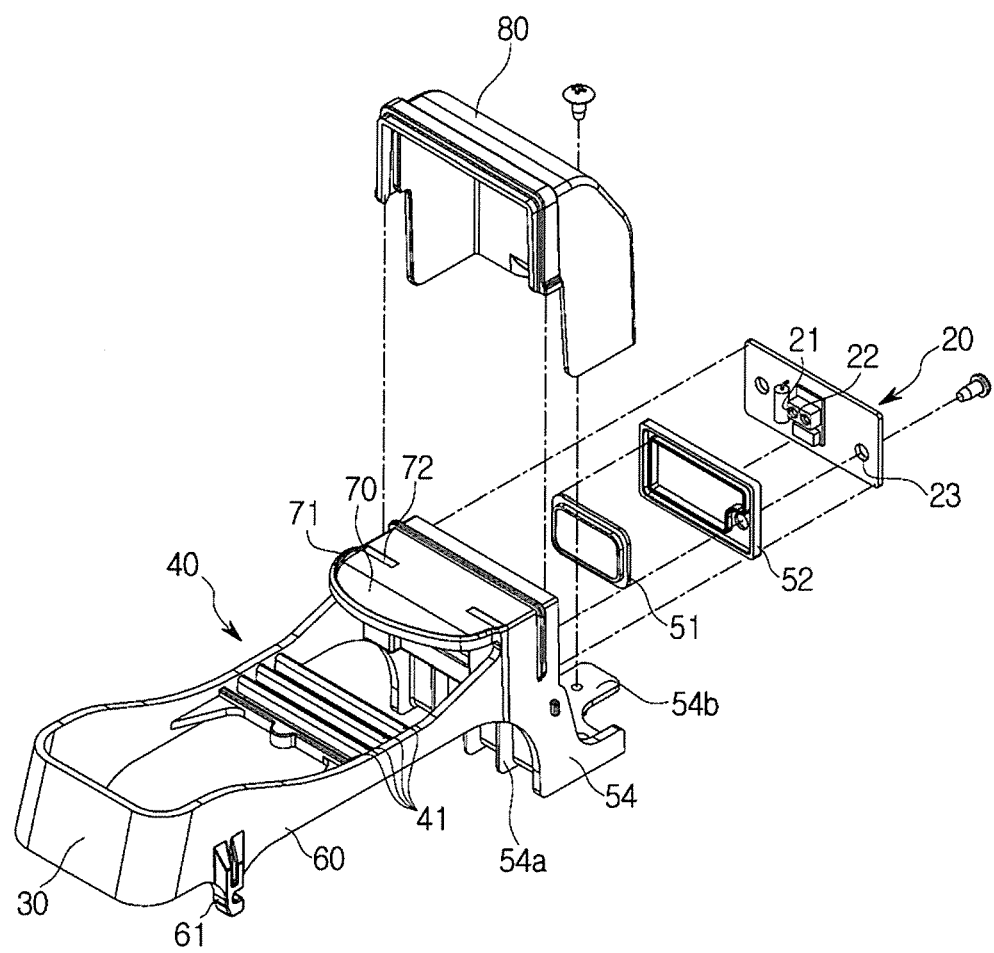
FIG. 7 illustrates the configuration of the detection device according to various embodiments of the present disclosure.
Figure 8:
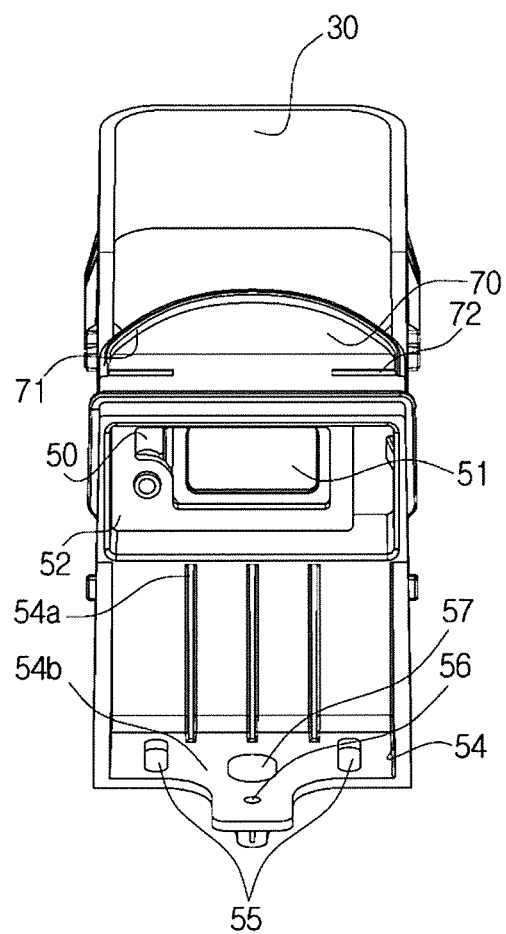
FIG. 8 illustrates the configuration of the detection device according to various embodiments of the present disclosure, viewed from a rear side.
Figure 9:
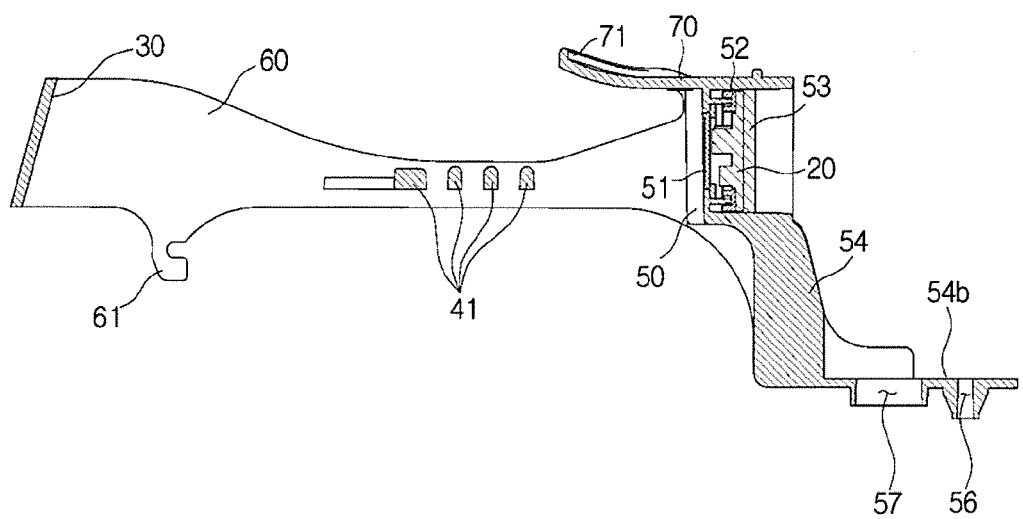
FIG. 9 illustrates the configuration of the detection device according to various embodiments of the present disclosure.

In addition, as illustrated in FIG. 5B, when the incidence angle and the reflection angle of the optical signals are increased by the interfering material, the optical signals may not be received by the light-receiving unit 22. In certain embodiments, the light-receiving unit 22 does not detect the value of the optical signals (b).

When snow piles up on the outdoor unit main body 1, in detail, when snow piles up on an optical path formed between the light-emitting unit 21, the reflecting plate 30 and the light-receiving unit 22 of the detection device 10 and interferes the optical signals, optical signals having a different value from the default value or no optical signals are received by the light-receiving unit 22.

As illustrated in FIGS. 6 through 9, the detection device 10 includes the optical sensor 20 to determine whether snow piles up on the outdoor unit main body 1 and a snow cover detection area 40 that is a space in which snow piles up, to determine whether snow cover occurs, through detection of the optical sensor 20.

The snow cover detection area 40 is disposed between the optical sensor 20 and the reflecting plate 30. When snow piles up in the snow cover detection area 40, a portion in which snow cover occurs, as described above, interferes the optical signals generated by the light-emitting unit 21, and the light-receiving unit 22 receives optical signals having a value different from the default value.

The snow cover detection area 40 is disposed in an upper side of the fan guard 6. This is to remove snow that piles up in the snow cover detection area 40 due to wind generated by the fan 4, when the fan 4 is driven by a controller 100 that will be described later.

A plurality of ribs 41 are disposed on a lower portion of the snow cover detection area 40. The plurality of ribs 41 are disposed to be spaced from each other.

A space in which the plurality of ribs 41 are disposed to be spaced from each other, is a ventilation path through which wind caused by the fan 4 passes. Due to wind that passes through the ventilation path, snow that piles up on the ribs 41 is removed.

In certain embodiments, snow that piles up on the fan guard 6 and the discharge port 1b also is removed in addition to snow that piles up in the snow cover detection area 40 by driving of the fan 4. The optical sensor 20 is seated on an optical sensor housing 50. The optical sensor housing 50 protects the optical sensor 20 and supports the reflecting plate 30.

A transparent member 51 through which the light-emitting unit 21 of the optical sensor 20 radiates optical signals and the light-receiving unit 22 receives the radiated optical signals, is disposed on at least a part of the front surface of the optical sensor housing 50.

The transparent member 51 and the optical sensor 20 are disposed in parallel to correspond to each other. A fixing member 52 is disposed between the transparent member 51 and the optical sensor 20 and fixes and supports the transparent member 51 and the optical sensor 20.

The fixing member 52 forms a hollow portion not to interfere radiation and receiving of the optical signals of the optical sensor 20 and is disposed to be in close contact with the transparent member 51 and the optical sensor 20.

Support protrusions (not shown) are disposed inside the optical sensor housing 50, and the optical sensor 20 is seated on the support protrusions. A fixing groove 23 is formed in one side of the optical sensor 20, passes through the fixing member 52, and is screw-coupled to the optical sensor housing 50.

A wire (not shown) that transmits the optical signals to the controller 100 and supplies power to the optical sensor 20 is disposed behind the optical sensor 20.

After the optical sensor 20 is coupled to the optical sensor housing 50 using a screw, a molding portion 53 molded with an epoxy is disposed behind the optical sensor 20. The molding portion 53 assists supporting of the optical sensor 20 when an epoxy is deposited in the optical sensor housing 50 and is coagulated. When an epoxy is deposited, the fixing member 52 prevents an epoxy liquid from penetrating into the front surface of the optical sensor 20.

A plurality of frames 60 are disposed on the front surface of the optical sensor housing 50 so that the optical sensor housing 50 and the reflecting plate 30 are connected to each other through the plurality of frames 60.

A pair of frames 60 are symmetrical to each other and connect the optical sensor 20 and the reflecting plate 30 so that the optical sensor 20 and the reflecting plate 30 is disposed to correspond to each other.

One side of each of the frames 60 extends from the front surface of the optical sensor housing 50, and the other side of each frame 60 is connected to a side of the reflecting plate 30 in a curve shape.

The frame 60 is not limited to various embodiments of the present disclosure but may extend as a single member, and two or more frames 60 extend up to the reflecting plate 30.

A plurality of ribs 41 extend to an inside of the pair of frames 60. The plurality of ribs 41 protrude toward a side in which the pair of frames 60 face each other and connect the frames 60.

A separation distance between the ribs 41 disposed most adjacent to the optical sensor 20 and the optical sensor 20 is formed to be longer than a minimum distance that is measured at least by the optical sensor 20.

When the separation distance between the ribs 41 disposed most adjacent to the optical sensor 20 and the optical sensor 20 is a distance that may not be measured by the optical sensor 20, although snow piles up in the snow cover detection area 40, the light-receiving unit 22 may not receive the optical signals, and the controller 100 may not determine whether snow cover occurs.

When a PSD sensor according to various embodiments of the present disclosure is used, the distance between the ribs 41 disposed most adjacent to the optical sensor 20 and the optical sensor 20 is equal to or greater than at least 40 mm.

In addition, when the PSD sensor is used, the separation distance between the optical sensor 20 and the reflecting plate 30 is formed to be longer than a minimum distance at which, when snow piles up in at least the snow cover detection area 40, it is detected that a value of optical signals obtained by the optical sensor 20 and a value of optical signals reflected from the reflecting plate 30 are different from each other.

When a PSD sensor according to various embodiments of the present disclosure is used, the separation distance between the reflecting plate 30 and the optical sensor 20 is equal to or greater than at least 150 mm.

A plate 70 is disposed on an upper side of the front surface of the optical sensor housing 50 in such a way that the optical sensor 20 radiates or receives the optical signals smoothly. This is to prevent the optical sensor 20 from being interfered by snow cover.

The plate 70 is disposed in a slope shape of a curved surface, one end of which is lifted upward, the one end having a shape of eaves in which the plate 70 directs outward from the front surface of the optical sensor housing 50.

A flange 71 that protrudes upward is continuously disposed at a boundary of the plate 70.

This is to prevent, when accumulated snow is changed into water due to phase conversion, water that remains in the plate 70 from dropping onto the front surface of the optical sensor housing 50. In addition, ice having an icicle shape is prevented from forming at the boundary of the plate 70.

The optical sensor housing 50 includes a drainage groove 72 that is formed from a side in which the optical sensor housing 50 and the plate 70 contact each other, toward a lower side of the optical sensor housing 50 so that moisture that remains in the plate 70 is drained toward a bottom end of the optical sensor housing 50.

This is to induce, when accumulated snow is changed into water due to phase conversion, water that remains in the plate 70 toward the lower side of the optical sensor housing 50.

As illustrated in FIG. 3, the detection device 10 is installed at the upper side of the outdoor unit main body 1 and is disposed to be separated from the outdoor unit main body 1. To this end, a coupling portion 61 is disposed at a lower side of the frame 60, and a fixing portion 54 is disposed at a lower side of the optical sensor housing 50.

The coupling portion 61 is disposed at the lower side of the frame 60 so that the fan guard 6 and the detection device 10 are coupled to each other. As described above, since the snow cover detection area 40 needs to be formed in the upper side of the fan guard 6, the frame 60 needs to be coupled to the fan guard 6.

Since the detection device 10 is installed in the outdoor unit main body 1 optionally according to the user's need, the detection device 10 is disposed to be separated from the outdoor unit main body 1.

The coupling portion 61 is formed to have a shape of a hook through which the fan guard 6 and the coupling portion 61 is easily coupled to or separated from each other. The grill portion of the fan guard 6 is seated inside the hook and is supported thereon. The hook portion is pressed to be separated from the grill portion as needed.

Since one side of the detection device 10 is disposed as the coupling portion 61 having the hook shape, the fixing portion 54 is disposed on the other side of the detection device 10 so that the detection device 10 is coupled to the outdoor unit main body 1.

The fixing portion 54 is disposed to extend toward a lower side of the optical sensor housing 50 and to be bent. A bent part of the fixing portion 54 includes a bracket 54b that faces the top end of the outdoor unit main body 1.

The fixing portion 54 extends toward the lower side of the optical sensor housing 50 to correspond to a height of the fan guard 6 disposed at an upper side of the outdoor unit main body 1.

In addition, a plurality of reinforcement ribs 54a are disposed on front and rear surfaces of the fixing portion 54 so as to reinforce rigidity of the fixing portion 54.

The bracket 54b includes a fixing protrusion 56 through which the bracket 54b and the outdoor unit main body 1 is coupled to each other.

The fixing protrusion 56 protrudes toward a lower side of the bracket 54b to have a cylindrical shape including a hollow portion. A groove (not shown) is formed in a position corresponding to the fixing protrusion 56 so that the fixing protrusion 56 is seated on the groove (not shown).

When the fixing protrusion 56 is seated, the fixing protrusion 56 and the groove (not shown) is coupled to each other using a screw so that the detection device 10 and the outdoor unit main body 1 is coupled to each other.

In addition, the bracket 54b includes a pair of slits 55, thereby preventing the detection device 10 from being rotated about the fixing protrusion 56 used as an axis. A long side is provided for the slits 55, and the user performs screw-coupling, whereby the upper side of the outdoor unit main body 1 passes through the slits 55, in an arbitrary position.

In addition, a connection hole 57 is formed in the bracket 54b so that a wire (not shown) that extends from a rear side of the optical sensor 20 is connected to an inside of the outdoor unit main body 1 through the connection hole 57. A hole (not shown) is formed in a side corresponding to the upper side of the outdoor unit main body 1 so that the connection hole 57 is seated in the hole (not shown).

A cover 80 is disposed at the rear side of the optical sensor housing 50 to protect the rear surface of the optical sensor housing 50, the wire (not shown) connected to the rear surface of the optical sensor housing 50, and the fixing portion 54.

The cover 80 is disposed to be detached from the detection device 10.

When coupling and separating the detection device 10 to and from the outdoor unit main body 1, the user separates the cover 80 from the detection device 10 so that an operation of separating the detection device 10 from the outdoor unit main body 1 is easily performed.

Hereinafter, a method of controlling an outdoor unit using the controller 100 that receives a measurement value of the detection device 10 will be described.

Figure 10:
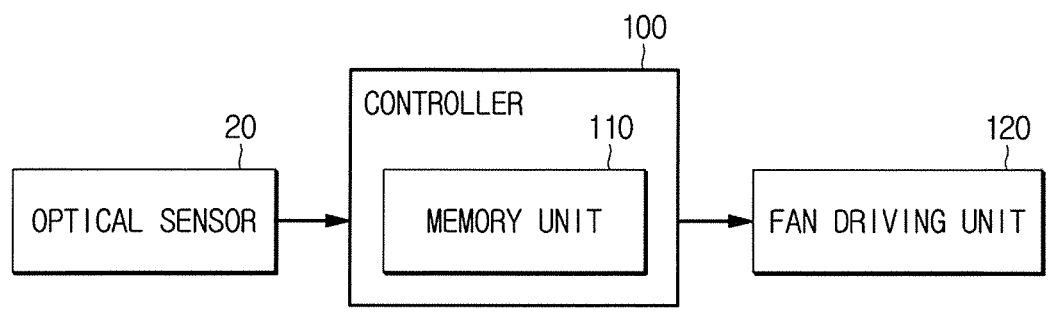
FIG. 10 illustrates a configuration for controlling the outdoor unit of the air conditioner according to various embodiments of the present disclosure.
Figure 11:
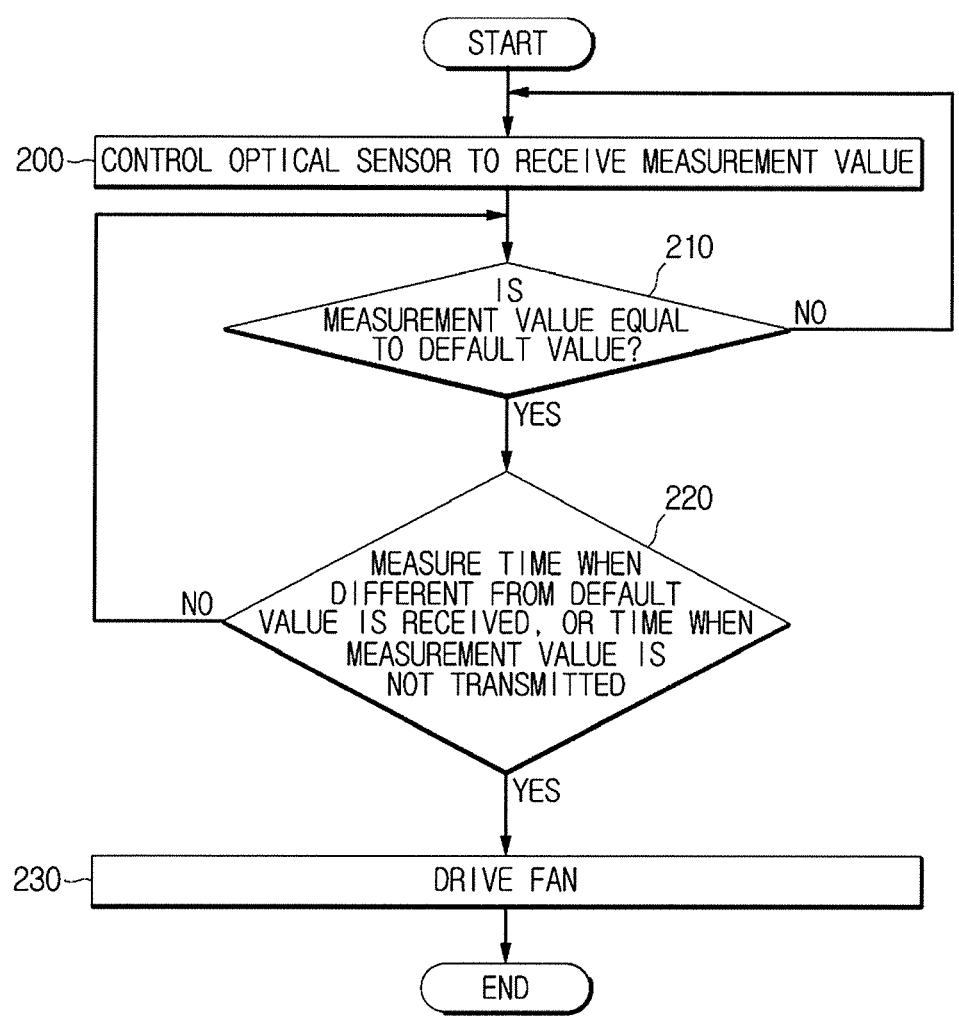
FIG. 11 illustrates a method of controlling the outdoor unit of the air conditioner according to various embodiments of the present disclosure.

As illustrated in FIGS. 10 and 11, in operation 200, the measurement value received from the optical sensor 20 is transmitted to the controller 100, and when a particular value is received, the controller 100 controls a fan driving unit 120 to drive the fan 4.

When snow cover does not occur in the outdoor unit, as illustrated in FIG. 4, the light-receiving unit 22 of the optical sensor 20 detects a default value that is obtained when the optical signals radiated from the light-emitting unit 21 are reflected from the reflecting plate 30 and are received.

The default value is stored in the memory unit 110 of the controller 100 and is used as a comparison reference regarding whether the controller 100 that will be described later drives the fan driving unit 120.

However, as illustrated in FIG. 4, when snow piles up on the outdoor unit main body 1 and snow cover occurs in the snow cover detection area 40, the optical signals radiated from the light-emitting unit 21 are reflected in the snow cover portion, and the optical signals are received by the light-receiving unit 22, and a value of the optical signals that is different from the default value is detected (a), or due to interference of the snow cover portion, the incidence angle and the reflection angle of the optical signals are increased so that the optical signals are not received by the light-receiving unit 22 and a value of the optical signals is not detected (b). The controller 100 controls the optical sensor 20 to receive the above-described measurement value in operation 200.

In operation 210, the controller 100 determines whether the measurement value received from the optical sensor 20 is compared with the default value stored in the memory unit 110 and is equal thereto.

When the measurement value received from the optical sensor 20 is equal to the default value, the controller 100 controllers the optical sensor 20 to receive the measurement value detected by the optical sensor 20 continuously.

However, in operation 220, when the measurement value received from the optical sensor 20 is different from the default value stored in the memory unit 110 or the optical sensor 20 does not transmit the measurement value, the controller 100 measures time when a value different from the default value is received, or time when the measurement value is not transmitted.

Although the different value from the default value is temporarily input to the controller 100 or the measurement value is not input to the controller 100, when a value transmitted from the optical sensor 20 is changed into the default value again, the controller 100 does not control the fan driving unit 130 but controls the optical sensor 20 and transmits the measurement value to the controller 100 continuously.

In operation 230, when the different value from the default value stored in the memory unit 110 is transmitted to the controller 100 for a predetermined time or the measurement value is not transmitted to the controller 100, the controller 100 controls the fan driving unit 130 to drive the fan 4.

In certain embodiments, the predetermined time is determined as time between 50 seconds and one minute.

When the fan 4 is driven by the fan driving unit 130 to generate wind for a predetermined time, snow that piles up in the snow cover detection area 40 is removed by driving of the fan 4.

In certain embodiments, snow that piles up in the snow cover detection area 40, the discharge port 1b and the fan guard 6 is removed so that the fan 4 is prevented from malfunctioning due to snow cover in advance.

After the fan 4 is driven for a predetermined time, the controller 100 controls the fan driving unit 130 to terminate driving of the fan 4.

Additionally, the controller 100 controls the optical sensor 20 continuously while the fan 4 is driven, and compares whether the measurement value transmitted from the optical sensor 20 coincides with the default value.

When the measurement value does not coincide with the default value, the fan driving unit 130 is controlled to drive the fan 4 continuously, and when the measurement value coincides with the default value, the fan driving unit 130 is controlled to terminate driving of the fan 4.

Hereinafter, another embodiment of the present disclosure will be described.

Another embodiment is only different from the above-described embodiment in that the light-emitting unit 21 and the light-receiving unit 22 of the optical sensor 20 are disposed to be spaced from each other. The difference will be described, and the description and reference numerals of the above-described embodiment are used for the same portions.

Figure 12:
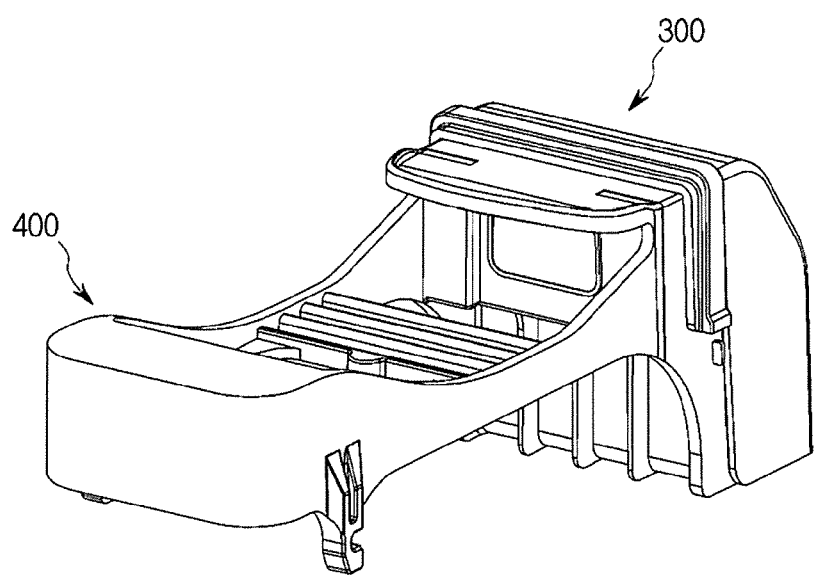
FIG. 12 illustrates a configuration of a detection device according to another embodiment of the present disclosure.
Figure 13:
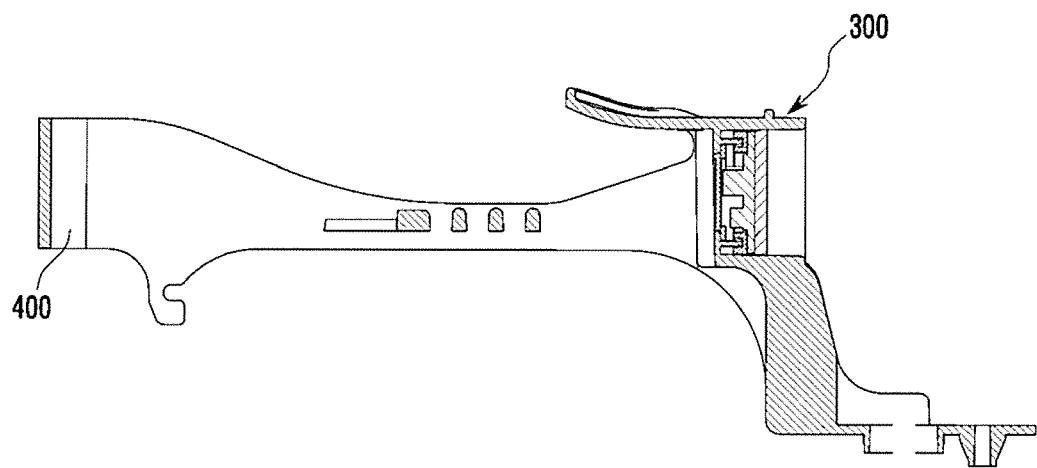
FIG. 13 illustrates the configuration of the detection device according to another embodiment of the present disclosure.

In addition, the same configuration as the above-described embodiment is not illustrated in FIGS. 12 and 13, and other configuration than a configuration having a difference that will be described later is the same as that of the drawings of the above-described embodiment.

According to another embodiment of the present disclosure, not the PSD sensor used in the above-described embodiment but the optical sensor 20 in which the light-emitting unit 21 and the light-receiving unit 22 are disposed to be spaced from each other, is used.

In certain embodiments, a distance measurement sensor that measures a distance is used as the optical sensor 20, and a sensor that determines only on or off whether light is received, is used as the optical sensor 20.

The default value detected by the optical sensor 20 is a measurement value of optical signals that are radiated from the light-emitting unit 21 and are received by the light-receiving unit 22 disposed to be spaced from the light-emitting unit 21.

An optical path according to various embodiments is formed not to pass through the reflecting plate 30 but to be connected directly to the light-receiving unit 22 from the light-emitting unit 21.

When a material is deposited between the light-emitting unit 21 and the light-receiving unit 22 and interference therebetween occurs, optical signals may not be received by the light-receiving unit 22, or optical signals having a different value from the default value is received by the light-receiving unit 22 by reflection.

In the current embodiment, since only a configuration including the light-emitting unit 21 and the light-receiving unit 22 is detected without using the reflecting plate 30, the reflecting plate 30 is not disposed, and each of the light-emitting unit 21 and the light-receiving unit 22 is disposed in a position in which the reflecting plate 30 and the optical sensor 20 according to the above-described embodiment are disposed.

A light-emitting unit housing 400 is disposed in a position of the reflecting plate 30 according to the above-described embodiment, and a light-receiving unit housing 300 is disposed in a position of the optical sensor housing 50. The light-receiving unit 22 is seated on the light-receiving unit housing 300, and the light-emitting unit 21 is seated on the light-emitting unit housing 400.

The configuration of the light-receiving unit housing 300 and the light-emitting unit housing 400 includes all of configurations required to seat the optical sensor 20, such as the transparent member 51, the fixing member 52, and the molding portion 53, as in the above-described embodiment.

A snow cover detection area 40 is formed between the light-receiving unit housing 300 and the light-emitting unit housing 400. When snow piles up in the snow cover detection area 40 due to snow cover, the snow cover portion is disposed on an optical path between the light-receiving unit 22 and the light-emitting unit 21. The optical signals received by the light-receiving unit 22 have a different value from the default value or are blocked so that the light-receiving unit 22 does not detect the optical signals.

When snow piles up in the snow cover detection area 40, the controller 100 detects whether snow piles up on the top end of the outdoor unit main body 1, controls the fan driving unit 120 to drive the fan 4.

As described above, when a detection device is disposed at an upper side of an outdoor unit of an air conditioner and a predetermined amount of snow piles up on the detection device, a value that is different from a default value is measured by a sensor of the detection device, and it can be determined whether snow cover occurs in the entire outdoor unit.

When a predetermined amount of snow piles up on the outdoor unit and signals are applied to a controller using the sensor, a fan of the outdoor unit operates and can prevent from malfunctioning.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An outdoor unit of an air conditioner, the outdoor unit comprising:
    an outdoor unit main body comprising a fan and a discharge port; and
    a detection device installed in the outdoor unit main body to detect snow that piles up on the outdoor unit main body,
    wherein the detection device comprises:
        an optical sensor comprising a light-emitting unit and a light-receiving unit;
        a reflecting plate disposed to be spaced from the optical sensor and configured to reflect optical signals radiated from the light-emitting unit; and
        a snow cover detection area disposed between the optical sensor and the reflecting plate.

2. The outdoor unit of claim 1, wherein the snow cover detection area is disposed in an upper side of the discharge port that is a ventilation path of the fan so that snow that piles up in the snow cover detection area is removed based on an operation of the fan.

3. The outdoor unit of claim 1, wherein the snow cover detection area comprises a plurality of ribs disposed on a bottom end of the snow cover detection area so that wind generated by an operation of the fan is able to pass through the snow cover detection area and remove accumulated snow.

4. The outdoor unit of claim 1, wherein the detection device comprises:
    an optical sensor housing on which the optical sensor is seated; and a pair of frames disposed to extend from one side of the optical sensor housing to the reflecting plate so that the optical sensor housing and the reflecting plate are connected to each other.

5. The outdoor unit of claim 4, wherein the snow cover detection area is disposed between the optical sensor housing and the reflecting plate to extend from one side of each of the frames.

6. The outdoor unit of claim 4, wherein each of the frames further comprises a coupling portion that extends to a lower side of the frame and is coupled to a fan guard so that one side of the detection device and the fan guard provided for the discharge port of the outdoor unit are coupled to each other.

7. The outdoor unit of claim 6, wherein the coupling portion is disposed to have a shape of a hook facing the lower side of the frame so that the fan guard and the detection device are able to be separated from each other.

8. The outdoor unit of claim 4, wherein the optical sensor housing comprises:
   a transparent member disposed to correspond to a front surface of the optical sensor; and
   a fixing member disposed to fix the front surface of the optical sensor and the transparent member.

9. The outdoor unit of claim 4, wherein the optical sensor housing further comprises a plate that extends from a top end of the optical sensor housing to a side that a front surface of the optical sensor faces so as to protect the front surface of the optical sensor.

10. The outdoor unit of claim 9, wherein the plate comprises a flange that protrudes to an upper side of a circumferential surface of the plate and is disposed to have a shape of a slope, one end of which facing an outside of the plate is lifted upward.

11. The outdoor unit of claim 9, wherein the plate comprises a drainage groove disposed from a side that contacts the optical sensor housing toward a lower side of the optical sensor housing so that water that remains in the plate is drained toward a bottom end of the optical sensor housing.

12. The outdoor unit of claim 4, wherein the optical sensor housing further comprises a fixing portion disposed to be fixed to an upper side of the outdoor unit.

13. The outdoor unit of claim 12, wherein the fixing portion comprises:
   a bracket that is bent and extends from a lower side of the optical sensor housing to face the upper side of the outdoor unit; and
   a plurality of slits through which the bracket passes and screw-coupled to the outdoor unit.

14. An outdoor unit for an air conditioner, the outdoor unit comprising:
   an outdoor unit main body comprising a fan and a discharge port; and
   a detection device installed to be separated from the outdoor unit main body and configured to detect snow that piles up on the outdoor unit main body,
   wherein the detection device comprises:
      an optical sensor comprising a light-emitting unit and a light-receiving unit; and
      a snow cover detection area disposed on an optical path in which optical signals radiated from the light-emitting unit reach the light-receiving unit,
      a reflecting late disposed the so that the optical path formed between the light-emitting unit and the light-receiving t is changed by reflecting optical signals generated by the light-emitting unit.

15. The outdoor unit of claim 14, wherein the light-emitting unit and the light-receiving unit are disposed to be spaced from each other, and
   the snow cover detection area is disposed between the light-emitting unit and the light-receiving unit.

16. The outdoor unit of claim 14, wherein the snow cover detection area comprises a plurality of ribs that are disposed on an upper portion of the discharge port so that accumulated snow is able to be removed based on an operation of the fan and that are disposed on a bottom end of the snow cover detection area so that wind generated by the fan is able to remove snow.

17. A method of controlling an outdoor unit of an air conditioner comprising an outdoor unit main body including a fan, the method comprising:
   radiating optical signals toward a reflecting plate using a light-emitting unit of an optical sensor;
   receiving the radiated optical signals, after reflecting off the reflecting plate, using a light-receiving unit of the optical sensor and measuring a distance of light movement;
   comparing the measured distance with a default value that is a distance value between the light-emitting unit and the reflecting plate; and
   when the measured distance is different from the default value or optical signals are not received by the light-receiving unit, driving the fan.

18. The method of claim 17, further comprising measuring time when a state in which the measured distance is different from the default value or no optical signals are received, is maintained.

19. The method of claim 18, wherein, when the measured time is equal to or greater than a reference time, the fan is driven.

20. The method of claim 17, further comprising stopping the fan when the optical signals received by the light-receiving unit regain the default value after the fan is driven.

* * * * *